United States Patent [19]

Bost

[11] Patent Number: 4,938,929
[45] Date of Patent: Jul. 3, 1990

[54] STOPPER PENETRATION AND PIPETTE SYSTEM

[76] Inventor: Charles H. Bost, 1520 Eckert Dr., Winter Haven, Fla. 33880

[21] Appl. No.: 222,028

[22] Filed: Jul. 21, 1988

[51] Int. Cl.$^5$ .................. B01L 11/00; B67D 5/00; G01N 1/00
[52] U.S. Cl. ............................ 422/100; 422/99; 422/102; 422/104; 73/864.86
[58] Field of Search ............ 422/99, 100, 101, 102, 422/104; 73/864.24, 864.23, 864.86, 864.87

[56] References Cited

U.S. PATENT DOCUMENTS

| 3,991,627 | 11/1976 | Laird et al. | 73/864.23 |
| 4,577,514 | 3/1986 | Bradley et al. | 422/101 |

FOREIGN PATENT DOCUMENTS

| 2504823 | 11/1982 | France | 422/102 |

*Primary Examiner*—Christine M. Nucker
*Assistant Examiner*—William H. Beisner
*Attorney, Agent, or Firm*—William M. Hobby, III

[57] ABSTRACT

A stopper penetration and pipette apparatus is provided for punching holes and placing sleeves in the stoppers of medical vials in combination with a pipette system designed for use in connection with sleeves placed in the stoppers. A base is provided with an upright member and a vial holding member which is slidably attached to the base so that a vial can be loaded in a vial holder and slipped into position for having a hole punched in the stopper. A mechanism is provided for driving a sleeve into the stopper held in a vial positioned in the vial holder to form an opening through the stopper and the pipette is shaped to fit through the sleeve in the stopper for adding or removing material from the vial without removing the stopper. The pipette is also shaped to form a pressure fitted seal with this opening of the stopper for sealing the vial for disposal or the like.

13 Claims, 2 Drawing Sheets

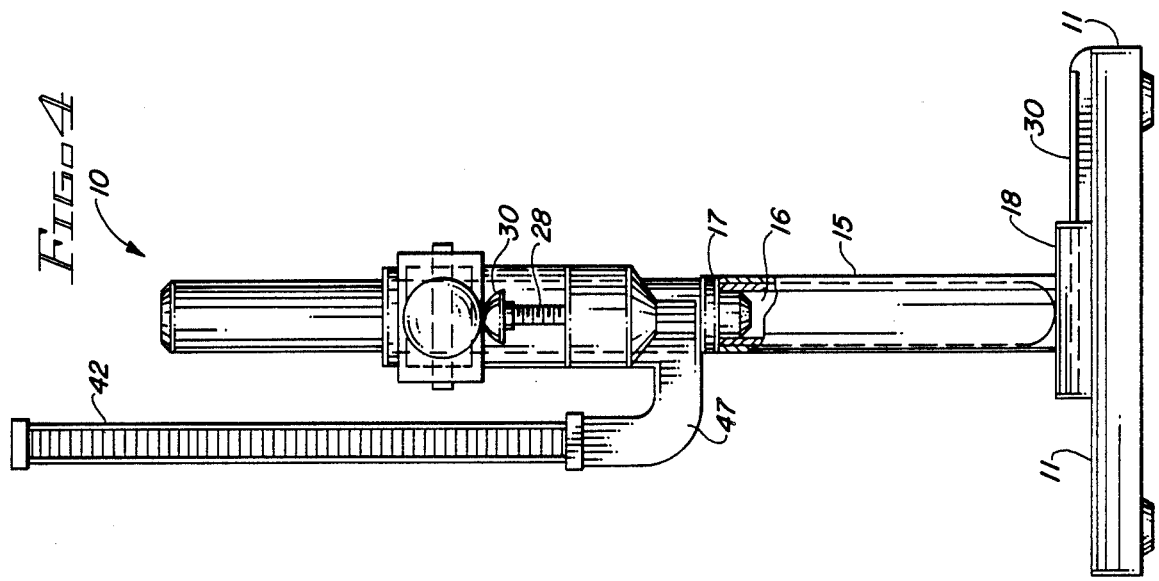
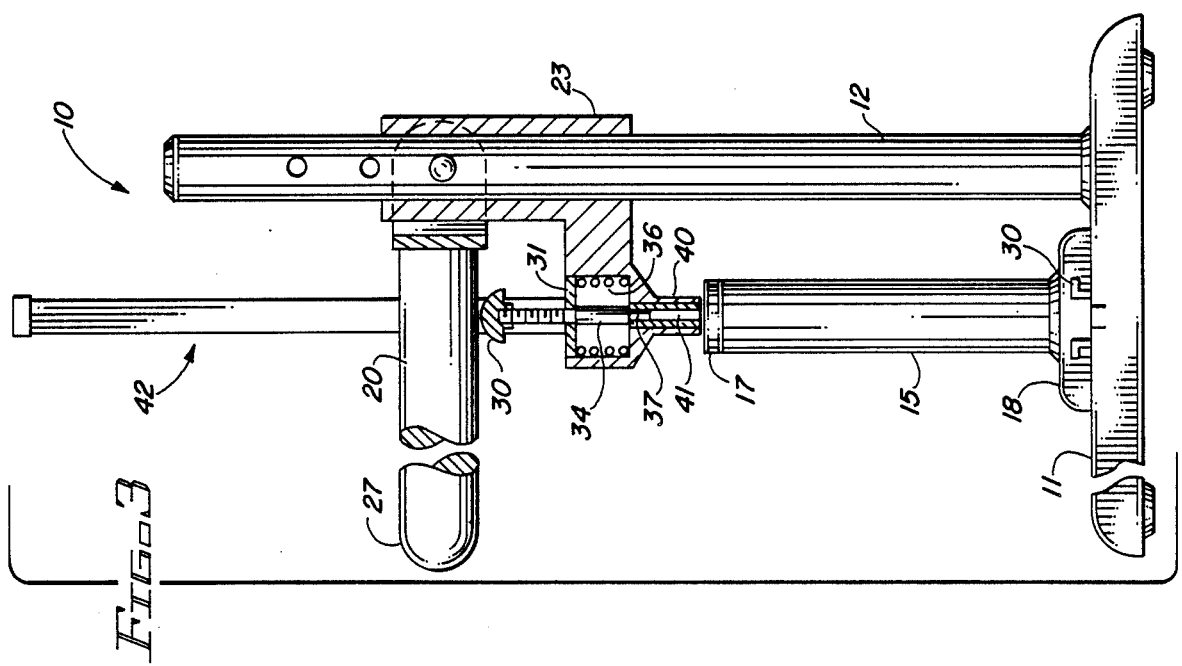
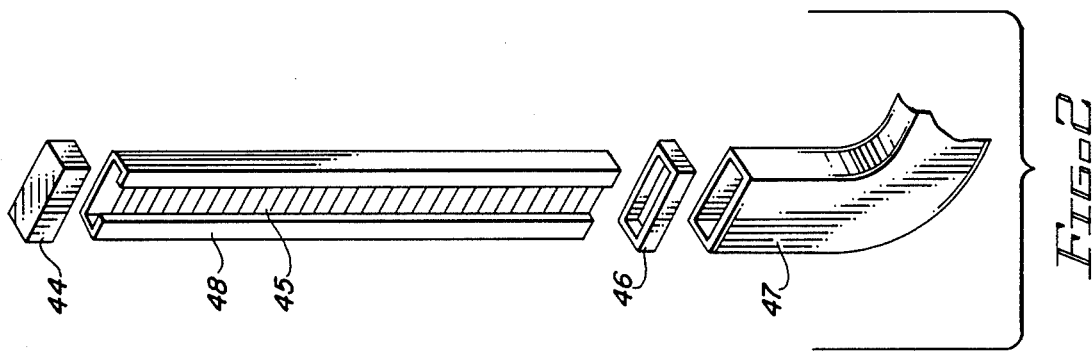

STOPPER PENETRATION AND PIPETTE SYSTEM

BACKGROUND OF THE INVENTION

The present invention relates to a mechanism for punching a hole in a stopper in combination with a pipette system for use with the opening punched in the stopper.

In the past hospitals and medical facilities have commonly obtained samples, such as blood samples, and placed them in vials with rubber stoppers covering the vials. The vials are labeled with the patient's information. The samples are then sent to a pathology department or to a lab to be analyzed. Once the blood samples are received in the lab the stoppers are removed and a pipette is used to remove small amounts of blood for placement on slides or in centrifuges or other laboratory devices for analyzing the blood. Blood may be analyzed through a microscope or may be centrifuged or may be analyzed with electrophorisis analysis. However blood, urine and other samples are sometimes contaminated with bacteria, viral or other microorganisms which are contagious and which may be contacted if the sample comes in contact with the medical personnel handling the sample. This can happen when the stopper is being removed from a vial if the blood splatters from the vial, or alternatively, if the vial breaks or from careless handling of the vial. Once the stopper is removed the pipette is then used to remove a portion of the sample for placing small amounts on slides for different tests.

The present invention is directed towards a system for removing the blood or other sample without removing the stopper placed therein with a pipette and then utilizing a specially designed pipette to seal the vial for disposal. This reduces the handling of the vial and the stopper and reduces the likelihood of the blood or other sample from getting on the skin of a lab or medical worker.

In the past other systems have been suggested for avoiding the splatter of blood in removing the stoppers from vials such as may be seen in my prior U.S. Pat. No.: 4,726,264 for a Stopper Removal Apparatus in which a specially designed cover is utilized for slipping over the stopper and shielding the stopper and vial from any splatter of blood or other liquids. The covers are throw away with the stopper or may be used to replace the stopper.

SUMMARY OF THE INVENTION

The present invention relates to a disposable stopper penetration system and a transfer pipette system in which the basic apparatus has a base with an upright frame member. A vial holding mechanism is attached to the base for holding the vial with a stopper therein and is slidable from a loading and unloading position to a position for driving a sleeve through the stopper. A mechanism is provided for driving a sleeve into the stopper held in a vial is positioned for driving a sleeve through the stopper held in the vial. A pipette is shaped to fit through the opening created by the sleeve driven through the vial for removing blood or other samples from the vial. The pipette is shaped to be attached to the stopper and sleeve by a pressure fit for resealing the vial for disposal.

The mechanism for driving a sleeve into the stopper includes a lever arm movably attached to the upright frame and positioned over a sleeve insertion member so that the lever arm can be driven against the sleeve insertion member to drive a sleeve held in a sleeve insertion guide into the stopper in a vial held in the vial holding mechanism. The lever arm is hinged to the upright frame member and may have a handle on one end for manually driving the plunger against the sleeve into the stopper. The mechanism for driving the sleeve into the stopper is adjustably attached to the upright frame member for different size vials and may have a magazine attached to feed individual sleeves into the sleeve guide. The plunger for driving the sleeves is spring loaded and is returned after each sleeve insertion. The lever driving arm may also be spring loaded to return to a position for driving the next sleeve into the next stoppered vial.

BRIEF DESCRIPTION OF THE DRAWINGS

Other objects, features and advantages of the present invention will be apparent from the written description and the drawings in which:

FIG. 2 is an exploded perspective of the magazine shown in the mechanism of FIG. 1;

FIG. 3 is a side sectional view of the mechanism of FIG. 1;

FIG. 4 is a front elevation of the mechanism of FIGS. 1 and 3;

DESCRIPTION OF THE PREFERRED EMBODIMENT

Figure 1:
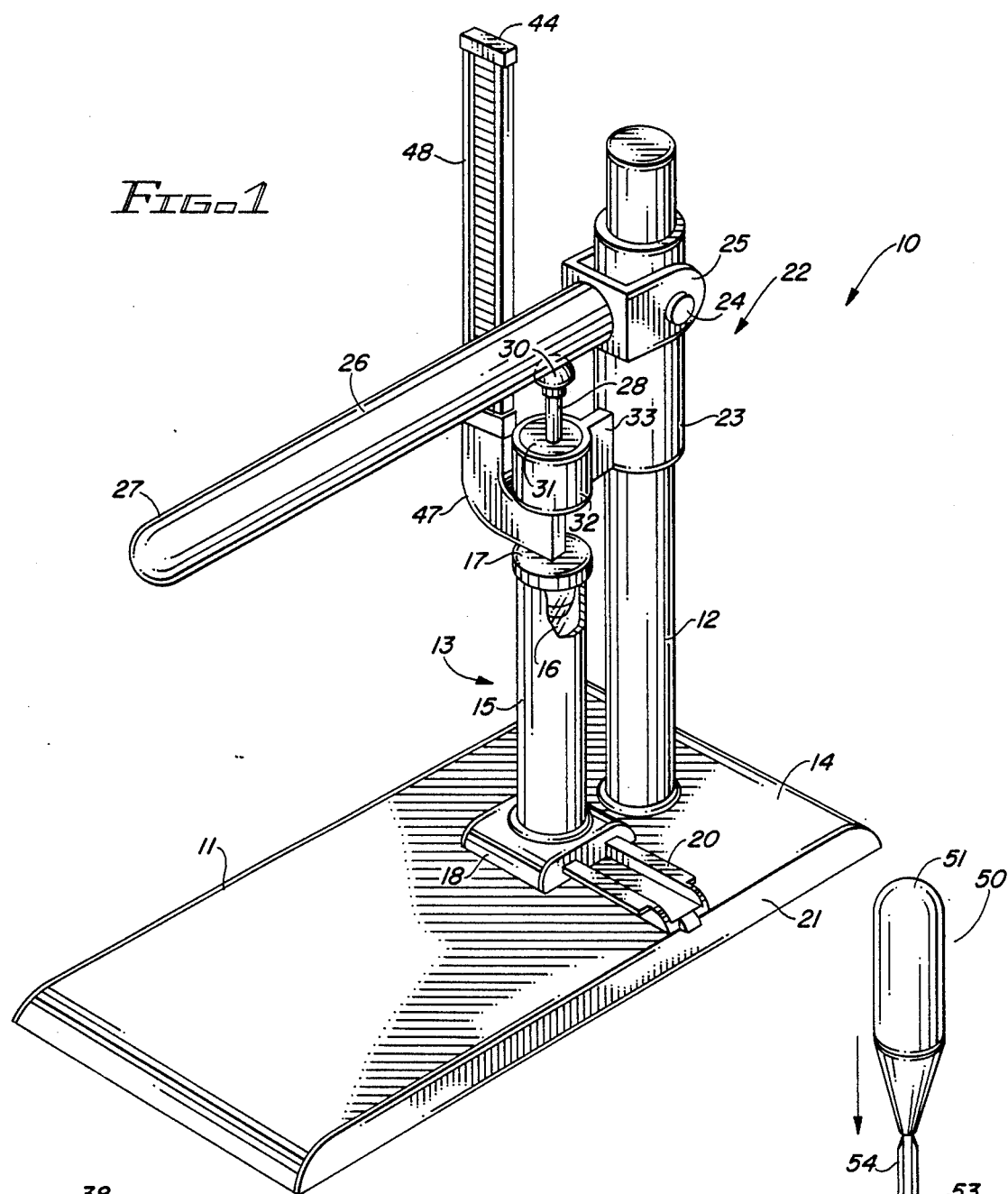
FIG. 1 is a perspective view of a disposable stopper penetration apparatus in accordance with the present invention.
Figure 5:
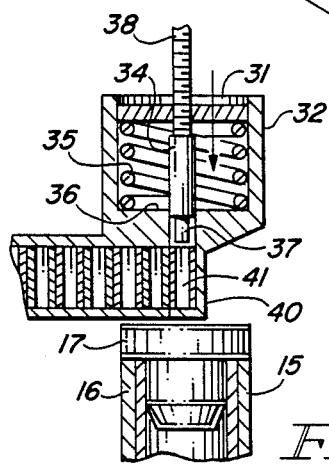
FIG. 5 is a sectional view taken through the circle 5 of FIG. 4.

Referring to the drawings and especially to FIGS. 1 through 5, a stopper penetration apparatus 10 is illustrated having a base with a vertical upright frame member 12. A vial holding mechanism 13 is attached to the top 14 of the base 11 and includes a vial holding sleeve 15 shown with a blood vial 16 therein stoppered with a stopper 17. The sleeve 15 is mounted to a sliding base 18 sliding in a track 20 from a plunger position as shown in FIG. 1 to a loading position abutting the edge 21 of the base 11. A vial 16 is thus loaded by sliding the base 18 on the track 20 to one side, putting the vial with the stopper 17 therein, sliding it to the position shown in FIG. 1 for driving (or punching) a sleeve into the stopper 17. A stopper penetration mechanism 22 has a sleeve 23 which slides on the vertical upright member 12 and is locked in a position with the hinge pin 24 passing through a lever handle yoke 25 through the sleeve 23 and through the vertical upright member 12. The yoke 25 has an extending lever arm 26 pinned with the hinge pin 24 to form a lever with the handle portion 27 mounted directly atop a plunger member 28 having a plunger head 30. The plunger member 28 is attached to a disk 31 riding in a sleeve 32 which is attached with a bar 33 to the sleeve 23. The sleeve 32 has a plunger extension 34 thereinside along with a spring 35 riding against an annular ledge 36 on one end and pushing against the disk 31 on the other end to drive the disk 31 to the top as shown in FIGS. 3 and 5. The plunger portion 34 has a sleeve insertion tip 37 having a smaller diameter than the plunger portion 34. The plunger portion 34 may be threaded with threads 38 as shown in FIGS. 3 and 5 for adjusting the position of the head 30 as well as the position of the plunger tip 37. The sleeve 32 has a sleeve guide 40 attached to the bottom thereof with a sleeve 41 shown mounted therein in FIGS. 3 and 5.

A magazine 42 can feed the sleeves to the sleeve guide 40. The magazine has the main vertical magazine portion 48 with a removable cap 44 which is removed for loading the sleeves 45 thereinto. The main magazine is attached with a support bracket 46 to a guide portion 47 for guiding each sleeve successively into the guide 40. Thus the weight of the sleeves 45 will drive each next sleeve 41 into the guide position 40 where it is driven by manually hitting or pushing on the handle 27 of the lever arm 26 to drive against the head 30 to drive the plunger 28 and 34 against the sleeve 41 to punch it into the stopper to open a small passageway of predetermined size directly through the stopper 17 mounted in the vial 16.

This is accomplished very rapidly by sliding the vial holder 13 to the loading position, putting a vial in the holder, sliding it to the stopper punch position, pushing down on the handle 27 to drive the next sleeve 41 into the stopper, then sliding the vial holder 13 to its loading and unloading position, removing the vial and inserting another stoppered vial. This can be done very rapidly if desired without the risk of splashing any of the sample material or blood held in the vial 16 on a lab technician or other person.

Figure 6:
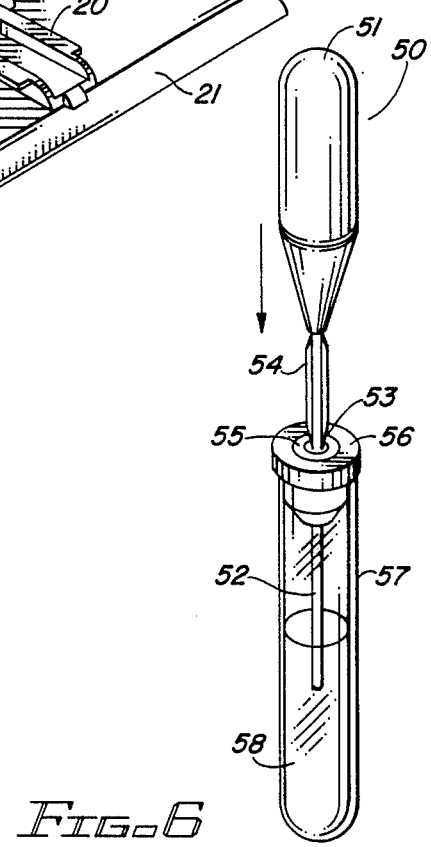
FIG. 6 is a perspective view of a stoppered vial having a sleeve punched therethrough and a pipette extending thereinto.

Once the sleeve has been driven through the stopper 17 the vial is removed and a specially designed pipette 50 shown in FIG. 6 has a handle portion 51 and an extending pipette tube 52 which angles out at 53 to a larger diameter 54. Alternatively, the pipettes can have a sleeve such as a rubber sleeve slid over the pipette tube 52 to provide the enlarged diameter area 54. The pipette is inserted into the sleeve 55 mounted in the stopper 56 in the vial 57 for removing some of the liquid 58 which is placed in small amounts on the various slides or sampling dishes for running the tests on the blood or other specimen. Once the tests have been run, the pipette 50 can be slid back into the sleeve 55 until the angled area 53 and enlarged diameter 54 press fit into the sleeve 55 to seal the vial 57, at which time it can be disposed of but has an air tight seal.

It should be clear at this time that a combination disposable stopper penetration or hole punch system and transfer pipette system have been provided which reduces the danger of dealing with large numbers of specimens or blood samples held in medical vials with stoppers. The invention does away with having to remove the stoppers and reduces the handling of the vials, and provides a safe way to reseal the vials. The stopper penetration mechanism 10 might typically be of metal components while the sleeves would typically be metal or plastic sleeves and can have a slightly tapered edge if desired. However it has been found that a sharpened edge is not needed for penetrating the stoppers in medical vials with a metal or plastic sleeve. Accordingly, the present invention is not to be limited to the forms shown which are to be considered illustrative rather than restrictive.

I claim:

1. A stopper penetration and pipette system comprising:
   a base;
   a vial holding means attached to said base for holding a vial to said base;
   means for driving a sleeve into a stopper held in a vial positioned in said vial holding means to thereby form an opening through said stopper of a predetermined size;
   magazine means for holding a plurality of sleeves and feeding one sleeve at a time to said means for driving a sleeve into a stopper held in a vial; and
   a pipette shaped to fit through said sleeve in said stopper; whereby material can be added to and removed from said vial without removing said stopper.

2. A stopper penetration and pipette system in accordance with claim 1 in which said pipette has means for attaching said pipette to said vial stopper whereby said pipette can be used to seal said vial.

3. A stopper penetration and pipette system in accordance with claim 2 in which said means for attaching said pipette to said vial stopper is a pipette shaped to be press fitted into said sleeve in said stopper when said pipette is pushed into said stopper sleeve a predetermined distance.

4. A stopper penetration and pipette system in accordance with claim 2 in which said means for attaching said pipette to said vial stopper includes a pipette stem of one diameter having an enlarged diameter along its length.

5. A stopper penetration and pipette system in accordance with claim 1 in which said base further includes an upright frame member.

6. A stopper penetration and pipette system in accordance with claim 5 in which said means for driving a sleeve into a stopper held in a vial positioned in said vial holding means further includes a lever driving arm movably attached to said upright frame member and positioned over a sleeve insertion member whereby said lever arm can be driven against said sleeve insertion member to drive said sleeve into said stopper.

7. A stopper penetration and pipette system in accordance with claim 6 in which said lever driving arm further includes a handle for manually driving a sleeve into a stopper.

8. A stopper penetration and pipette system in accordance with claim 7 in which said sleeve insertion member is spring loaded to return said sleeve insertion member when said lever arm is released.

9. A stopper penetration and pipette system in accordance with claim 8 in which said lever driving arm is adjustably attached to said upright frame member whereby said lever driving arm can be positioned for different sized vials.

10. A stopper penetration and pipette system in accordance with claim 9 in which said sleeve insertion member further includes a sleeve insertion guide member for guiding a sleeve into a stopper.

11. A stopper penetration and pipette system in accordance with claim 10 in which said magazine means is attached to said sleeve insertion guide member for feeding sleeves to said sleeve insertion guide member for insertion into a stopper.

12. A stopper penetration and pipette system in accordance with claim 10 in which sleeve insertion member is held in a sleeve insertion guide frame for guiding said sleeve insertion member onto a sleeve.

13. A stopper penetration and pipette system in accordance with claim 12 in which said sleeve insertion guide frame for guiding said sleeve insertion member into a sleeve has a spring mounted therein to provide said spring loading for said sleeve insertion member.

* * * * *